(12) United States Patent
Fischer et al.

(10) Patent No.: US 12,159,130 B2
(45) Date of Patent: Dec. 3, 2024

(54) ACQUIRING USER-SPECIFIC CUSTOMIZATION DATA FOR A MEDICAL DEVICE

(71) Applicants: Fresenius Medical Care Deutschland GmbH, Bad Homburg (DE); Fresenius Medical Care Holdings, Inc., Waltham, MA (US)

(72) Inventors: Karsten Fischer, Waltham, MA (US); Stefan Perplies, Schweinfurt (DE)

(73) Assignees: Fresenius Medical Care Deutschland GmbH, Bad Homburg (DE); Fresenius Medical Care Holdings, Inc., Waltham, MA (US)

( * ) Notice: Subject to any disclaimer, the term of this patent is extended or adjusted under 35 U.S.C. 154(b) by 361 days.

(21) Appl. No.: 17/383,524

(22) Filed: Jul. 23, 2021

(65) Prior Publication Data
US 2023/0022816 A1 Jan. 26, 2023

(51) Int. Cl.
*G06F 8/65* (2018.01)
*G06F 3/0481* (2022.01)
(Continued)

(52) U.S. Cl.
CPC .............. *G06F 8/65* (2013.01); *G06F 3/0481* (2013.01); *G06F 9/4451* (2013.01); *G06F 9/451* (2018.02); *G16H 10/65* (2018.01); *G16H 40/40* (2018.01); *G16H 40/60* (2018.01); *G16H 40/63* (2018.01); *H04L 63/08* (2013.01); *A61M 1/14* (2013.01); *H04L 2463/082* (2013.01)

(58) Field of Classification Search
CPC ........ G16H 40/40; G16H 40/63; G16H 40/65; G16H 10/60; G16H 40/60; G16H 10/65; A61M 1/282; A61M 1/14; G06F 19/322; G06F 8/65; G06F 19/3406; G06F 9/4451; G06F 3/0481; G06F 9/451; H04L 63/08; H04L 2463/082
See application file for complete search history.

(56) References Cited

U.S. PATENT DOCUMENTS 9,690,538 B1 * 6/2017 Doyle, III ............. H04W 4/023
10,042,979 B2 * 8/2018 Moore .................... G16Z 99/00
(Continued)

FOREIGN PATENT DOCUMENTS

JP 2011039624 A * 2/2011
WO WO-9640317 A1 * 12/1996 .......... A61M 1/1686
WO WO-2015031861 A1 * 3/2015 .......... B60R 16/037

*Primary Examiner* — Andrew L Tank
(74) *Attorney, Agent, or Firm* — Fish & Richardson P.C.

(57) ABSTRACT

A computer-implemented method, a medical device, and a system for acquiring user-specific customization data, i.e. user-specific language packages, are provided. The computer-implemented method comprises: determining a first set of user-specific customization data stored on the medical device; comparing the first set of user-specific customization data with a second set of user-specific customization data that is required by a user; and upon determining that the second set of user-specific customization data is different from the first set of user-specific customization data, acquiring, from a data storage external to the medical device, the second set of user-specific customization data or a delta between the first set and the second set of user-specific customization data.

20 Claims, 2 Drawing Sheets

Figure 1:
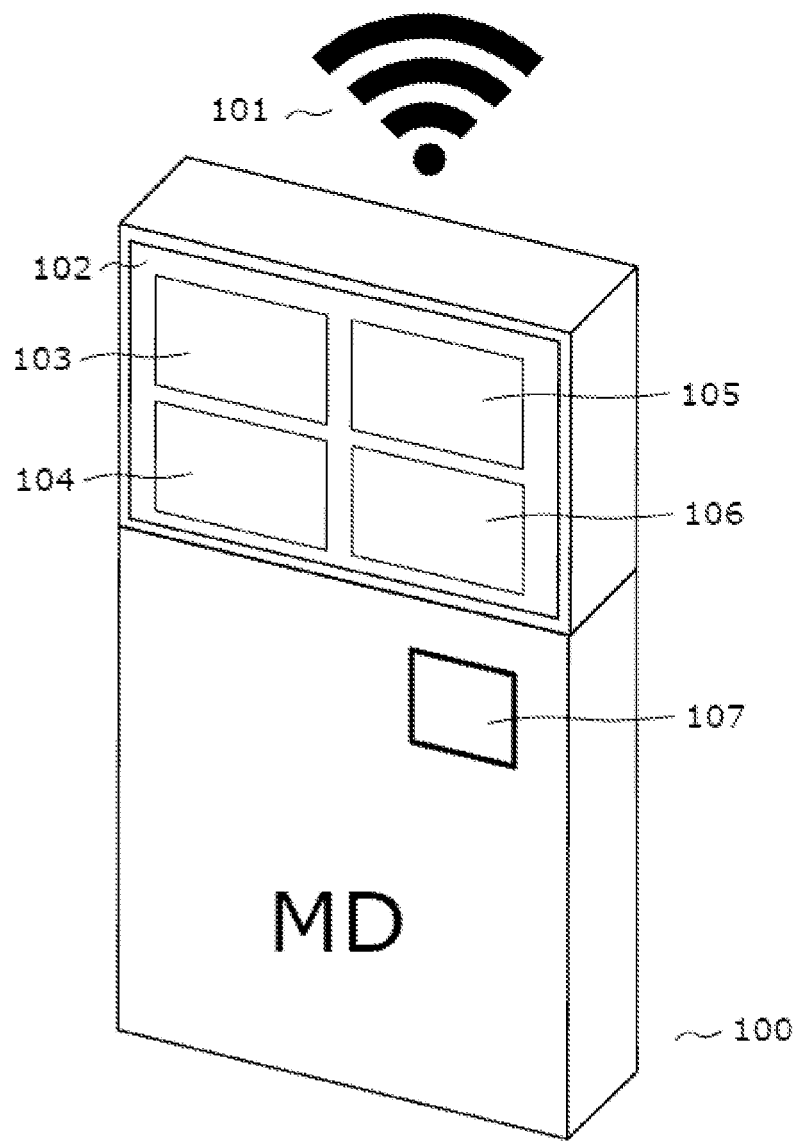

(51) Int. Cl.
  *G06F 9/445* (2018.01)
  *G06F 9/451* (2018.01)
  *G16H 10/65* (2018.01)
  *G16H 40/40* (2018.01)
  *G16H 40/60* (2018.01)
  *G16H 40/63* (2018.01)
  *H04L 9/40* (2022.01)
  *A61M 1/14* (2006.01)

(56) References Cited

U.S. PATENT DOCUMENTS

| | | | |
|---|---|---|---|
| 10,915,306 B2* | 2/2021 | Jain | G06F 3/04817 |
| 11,260,153 B2* | 3/2022 | Tiwari | A61M 1/36 |
| 11,361,266 B2* | 6/2022 | Miller | G06Q 10/063114 |
| 2003/0212438 A1* | 11/2003 | Nova | G16Z 99/00 |
| | | | 607/30 |
| 2007/0282912 A1* | 12/2007 | Reiner | G16H 30/40 |
| 2008/0314973 A1* | 12/2008 | Zuhars | G16H 40/40 |
| | | | 705/2 |
| 2009/0150416 A1* | 6/2009 | Baker | G16H 10/60 |
| 2009/0228877 A1* | 9/2009 | Duan | H04L 67/34 |
| | | | 713/1 |
| 2011/0246220 A1* | 10/2011 | Albert | G06Q 10/00 |
| | | | 705/2 |
| 2013/0133055 A1* | 5/2013 | Ali | H04L 63/0861 |
| | | | 726/7 |
| 2013/0310726 A1* | 11/2013 | Miller | G16H 40/63 |
| | | | 717/173 |
| 2016/0012184 A1* | 1/2016 | Nimmagadda | G06F 8/65 |
| | | | 705/3 |
| 2017/0017479 A1* | 1/2017 | Hedmann | G06F 21/31 |
| 2017/0065757 A1* | 3/2017 | Tanenbaum | G16H 20/40 |
| 2017/0168688 A1* | 6/2017 | Yuds | G06V 40/172 |
| 2020/0221990 A1* | 7/2020 | Chiofolo | G06N 3/02 |
| 2021/0093764 A1* | 4/2021 | Merics | H04W 12/08 |
| 2021/0142912 A1* | 5/2021 | Belliveau | H04W 12/065 |

* cited by examiner

ACQUIRING USER-SPECIFIC CUSTOMIZATION DATA FOR A MEDICAL DEVICE

1. TECHNICAL FIELD

The present invention relates, in general, to customization of medical devices and, more particularly, to a computer-implemented method and a system for acquiring user-specific customization data, i.e. user-specific language packages on various medical devices.

2. BACKGROUND

In the future, data size of language packages will drastically increase as they shall comprise both text and speech data for supporting natural-language applications. Therefore, storing all types of language data on multiple devices is not memory efficient. In many cases, moreover, device users need to select desired language package or customization settings by hand, which is time-consuming and not efficient when switching the device. Therefore, customization procedures must be repeated so that additional time is required. In stressful situations and/or areas such as nursing homes and/or clinics, e.g., within Intensive Care Units (ICUs), time is a critical and valuable resource, which should be invested with care and in the best way serving the patients undergoing lifesaving medical treatments. Patients, on the other hand, receiving life-saving treatments at home, e.g., patients undergoing Peritoneal Dialysis (PD) and/or Hemodialysis (HD) at home, invest a large fraction of their time in treatment procedures. Due to treatment and/or prescription changes, medical devices need sometimes to be replaced so that patients and/or technical assistants must reconfigure the medical-device settings such as the system language. Since such language packages will require a large amount of device storage, it is not feasible to store all available language packages on the medical device. As customization procedures are time-consuming, patients need to spend additional time on such processes.

Therefore, the present invention aims to address these deficiencies and to provide a resource-efficient customization process for medical devices.

3. SUMMARY OF THE INVENTION

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

One or more of these objects are achieved by the subject matter of the independent claims. Preferred embodiments are subject of the dependent claims.

A $1^{st}$ embodiment of the invention is a computer-implemented method for resource-efficient customization of an operating system of a medical device, the method comprising:
  determining a first set of user-specific customization data stored on the medical device;
  comparing the first set of user-specific customization data with a second set of user-specific customization data that is required by a user;
  upon determining that the second set of user-specific customization data is different from the first set of user-specific customization data, acquiring, from a data storage external to the medical device, the second set of user-specific customization data or a delta between the first set and the second set of user-specific customization data.

According to a $2^{nd}$ embodiment, in the $1^{st}$ embodiment, the computer-implemented method further comprises storing the acquired user-specific customization data on a data storage of the medical device.

According to a $3^{rd}$ embodiment, in the $1^{st}$ or the $2^{nd}$ embodiment, the computer-implemented method further comprises reading the acquired user-specific customization data and customizing the operating system of the medical device based at least on the acquired user-specific customization data.

According to a $4^{th}$ embodiment, in any of the $1^{st}$ to the $3^{rd}$ embodiment, the data storage external to the medical device comprises a remote server, a data cloud, and/or a token, wherein the token is or comprises a USB drive, a smart card, a hard-disk drive, and/or a solid state disk.

According to a $5^{th}$ embodiment, in any of the $1^{st}$ to the $4^{th}$ embodiment, at least a part of the user-specific customization data is stored on a token, and wherein the step of acquiring comprises reading the token for acquiring the second set of user-specific customization data or the delta between the first set and the second set of user-specific customization data.

According to a $6^{th}$ embodiment, in any of the $1^{st}$ to the $5^{th}$ embodiment, user-specific customization data comprises language data, graphical user-interface elements, user-specific functions and/or any combination thereof.

According to a $7^{th}$ embodiment, in the $6^{th}$ embodiment, the language data comprises text and sound.

According to a $8^{th}$ embodiment, in the $6^{th}$ or the $7^{th}$ embodiment, the graphical user-interface elements comprise texts, buttons, sounds, colors, and/or graphical layouts, and wherein at least a part of the texts, buttons, sounds, colors, and/or graphical layouts is user-specific.

According to a $9^{th}$ embodiment, in any of the $6^{th}$ to the $8^{th}$ embodiment, the user-specific functions comprise user-specific system rights for controlling the medical device According to a $10^{th}$ embodiment, in any of the $1^{st}$ to the $9^{th}$ embodiment, the computer-implemented method further comprises verifying an identity of the user, before, during, and/or after the steps mentioned in the $1^{st}$ embodiment.

According to a $11^{th}$ embodiment, in the loth embodiment, verifying the identity of the user occurs before the steps mentioned in the $1^{st}$ embodiment, and wherein the steps mentioned in the $1^{st}$ embodiment are automatically triggered in response to verifying the identity of the user.

According to a $12^{th}$ embodiment, in the $10^{th}$ or the $11^{th}$ embodiment, verifying the identity of the user is performed via an authentication device of the medical device, the authentication device being or comprising a smartcard reader, an RFID/NFC reader, a QR code reader, a barcode reader, a USB port, a fingerprint sensor, a retina scanner, a microphone and/or a camera.

According to a $13^{th}$ embodiment, in any of the loth to the $12^{th}$ embodiment, verifying the identity of the user is based on multi-factor authentication.

According to a $14^{th}$ embodiment, in any of the loth to the $13^{th}$ embodiment, the computer-implemented method further comprises reading a user profile after verifying the identity of the user, wherein the user profile comprises information of the second set of user-specific customization data that is required by the user; and wherein, preferably, the steps mentioned in the $1^{st}$ embodiment are automatically triggered in response to reading the information of the second set of user-specific customization data from the user profile.

According to a 15th embodiment, in any of the 1st to the 14th embodiment, the medical device is configured to provide a renal replacement therapy to a patient, including one or more of Peritoneal Dialysis, Hemodialysis, Hemofiltration, and/or Hemodiafiltration.

According to a 16th embodiment, in any of the 1st to the 15th embodiment, the computer-implemented method further comprises reading log-in information from the user, wherein the steps mentioned in the 1st embodiment are triggered in response to the user having logged in for the first time at the medical device.

According to a 17th embodiment, in the 16th embodiment, reading the log-in information comprises reading the log-in information via a log-in screen provided by a display of the medical device, and wherein the log-in screen is displayed when the medical device is started and/or woken up from hibernation.

According to a 18th embodiment, in any of the 1st to the 17th embodiment, the computer-implemented method further comprises providing, by a display of the medical device, different sets of user-specific customization data for the user to select from, wherein the second set of user-specific customization data is the set of user-specific customization data selected by the user.

A 19th embodiment of the invention is a medical device for resource-efficient customization of an operating system running on the medical device, comprising:
  a processor;
  a memory; and
  computer-readable instructions stored in the memory and executable by the processor to:
    determine a first set of user-specific customization data stored on the medical device;
    compare the first set of user-specific customization data with a second set of user-specific customization data that is required by a user; and
    upon determining that the second set of user-specific customization data is different from the first set of user-specific customization data, acquire, from a data storage external to the medical device, the second set of user-specific customization data or a delta between the first set and the second set of user-specific customization data.

According to a 20th embodiment, in the 19th embodiment, the medical device further comprises computer-readable instructions stored in the memory and executable by the processor to store the acquired user-specific customization data on a data storage of the medical device.

According to a 21st embodiment, in the 19th or the 20th embodiment, the medical device further comprises computer-readable instructions stored in the memory and executable by the processor to read the acquired user-specific customization data and customize the operating system of the medical device based at least on the acquired user-specific customization data.

According to a 22nd embodiment, in any of the 19th to the 21st embodiment, the data storage external to the medical device comprises a remote server, a data cloud, and/or a token, wherein the token is or comprises a USB drive, a smart card, a hard-disk drive, and/or a solid state disk.

According to a 23rd embodiment, in any of the 19th to the 22nd embodiment, at least a part of the user-specific customization data is stored on a token, and wherein the step of acquiring comprises reading the token for acquiring the second set of user-specific customization data or the delta between the first set and the second set of user-specific customization data.

According to a 24th embodiment, in any of the 19th to the 23rd embodiment, user-specific customization data comprises language data, graphical user-interface elements, user-specific functions and/or any combination thereof.

According to a 25th embodiment, in the 24th embodiment, the language data comprises text and sound.

According to a 26th embodiment, in the 24th or the 25th embodiment, the graphical user-interface elements comprise texts, buttons, sounds, colors, and/or graphical layouts, and wherein at least a part of the texts, buttons, sounds, colors, and/or graphical layouts is user-specific.

According to a 27th embodiment, in any of the 24th to the 26th embodiment, the user-specific functions comprise user-specific system rights for controlling the medical device According to a 28th embodiment, in any of the 19th to the 27th embodiment, the medical device further comprises computer-readable instructions stored in the memory and executable by the processor to verify an identity of the user, before, during, and/or after the steps mentioned in the 19th embodiment.

According to a 29th embodiment, in the 28th embodiment, verifying the identity of the user occurs before the steps mentioned in the 19th embodiment, and wherein the steps mentioned in the 19th embodiment are automatically triggered in response to verifying the identity of the user.

According to a 30th embodiment, in the 28th or the 29th embodiment, verifying the identity of the user is performed via an authentication device of the medical device, the authentication device being or comprising a smartcard reader, an RFID/NFC reader, a QR code reader, a barcode reader, a USB port, a fingerprint sensor, a retina scanner, a microphone and/or a camera.

According to a 31st embodiment, in any of the 28th to the 30th embodiment, verifying the identity of the user is based on multi-factor authentication.

According to a 32nd embodiment, in any of the 28th to the 31st embodiment, the medical device further comprises computer-readable instructions stored in the memory and executable by the processor to read a user profile after verifying the identity of the user, wherein the user profile comprises information of the second set of user-specific customization data that is required by the user; and wherein, preferably, the steps mentioned in the 19th embodiment are automatically triggered in response to reading the information of the second set of user-specific customization data from the user profile.

According to a 33rd embodiment, in any of the 19th to the 32nd embodiment, the medical device is configured to provide a renal replacement therapy to a patient, including one or more of Peritoneal Dialysis, Hemodialysis, Hemofiltration, and/or Hemodiafiltration.

According to a 34th embodiment, in any of the 19th to the 33rd embodiment, the medical device further comprises computer-readable instructions stored in the memory and executable by the processor to read log-in information from the user, wherein the steps mentioned in the 19th embodiment are triggered in response to the user having logged in for the first time at the medical device.

According to a 35th embodiment, in the 34th embodiment, reading the log-in information comprises reading the log-in information via a log-in screen provided by a display of the medical device, and wherein the log-in screen is displayed when the medical device is started and/or woken up from hibernation.

According to a 36th embodiment, in any of the 19th to the 35th embodiment, the medical device further comprises computer-readable instructions stored in the memory and executable by the processor to provide by a display of the medical device, different sets of user-specific customization data for the user to select from, wherein the second set of user-specific customization data is the set of user-specific customization data selected by the user.

A 37th embodiment of the invention is a connected-health system for resource-efficient customization of an operating system running on a medical device, comprising:
 a data storage external to the medical device; and
 the medical device in accordance with any one of the medical device of the 19th to the 36th embodiment.

4. BRIEF DESCRIPTION OF THE DRAWINGS

Figure 2:
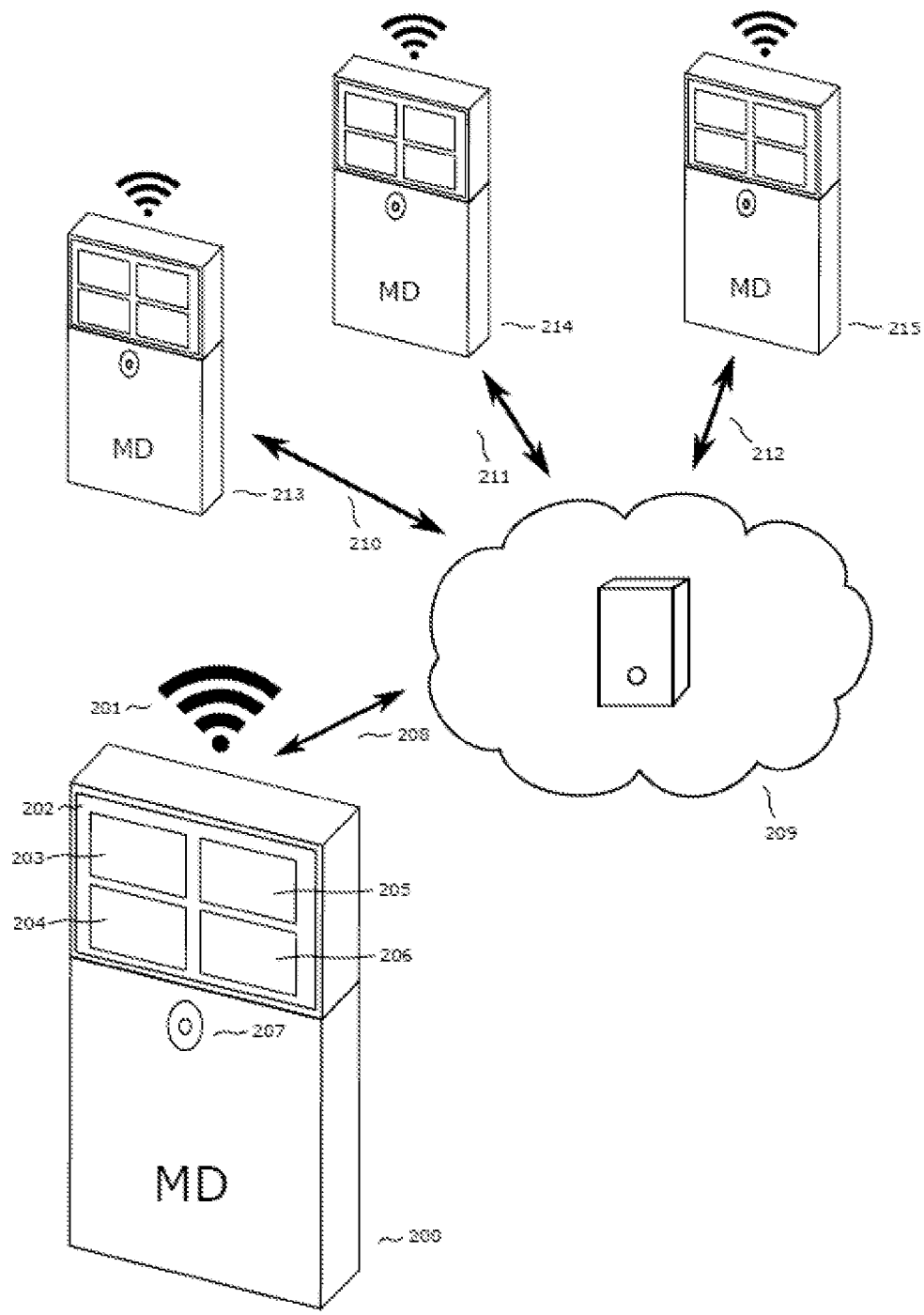

In the following, preferred embodiments of the present invention will be explained with reference to the accompanying figures:

FIG. 1: a schematic illustration of a medical device, which is designed to perform the computer-implemented method according to the present invention; and FIG. 2: an exemplary implementation of the connected-health system according to the present invention.

5. DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

FIG. 1 illustrates an example implementation of a medical device 100 according to the present invention. A medical device may be any device intended to be used for medical purposes. Medical devices according to the present invention may benefit patients by helping health care providers diagnose and/or treat patients and/or helping patients overcome sickness or disease, improving their quality of life. In particular, a medical device according to the invention may refer to any instrument, apparatus, appliance, software, material or other article, whether used alone or in combination, including the software intended by its manufacturer to be used specifically for diagnostic and/or therapeutic purposes and necessary for its proper application, intended by the manufacturer to be used for human beings for the purpose of:
 diagnosis, prevention, monitoring, treatment or alleviation of disease,
 diagnosis, monitoring, treatment, alleviation of or compensation for an injury or handicap,
 investigation, replacement or modification of the anatomy or of a physiological process, and/or
 control of conception, and which does not achieve its principal intended action in or on the human body by pharmacological, immunological or metabolic means, but which may be assisted in its function by such means.

The medical device 100 comprises at least a processor, at least a memory and computer-readable instructions stored in the memory and executable by the processor to perform a computer-implemented method according to the present invention for resource-efficient, e.g., memory-efficient, customization of the medical device.

In one embodiment, the medical device 100 may be a device for providing renal replacement therapy like Hemodialysis or Peritoneal dialysis. Since the disclosed method is not limited to dialysis devices, further medical devices having frequently changing medical personnel like infusion pumps, ventilators, and/or imaging devices like X-ray devices, CATs, and/or NMRI scanners, can also profit from the disclosed technical teaching.

In another embodiment, the medical device 100 may further comprise a network adapter such as a Wi-Fi network adapter 101 for communicating with a local and/or a wide area network. In some implementations, the network adapter may be any type of network adapter capable of connecting the medical device with a local and/or wide area network using wired and/or wireless communication, including, but not limited to Bluetooth, LTE, 5G, Zigbee, and/or Ethernet. In another implementation, the network adapter may be a second device external to medical device, wherein the medical device may comprise connection means, including, but not limited to USB and/or RS-232, configured to connect the medical device with the external network adapter.

In another embodiment, the medical device 100 may further comprise a display 102 such an LCD screen for outputs generated by an operating system of the medical device 100. The display 102 may further comprise a touch-sensitive input interface for controlling the medical device. In some implementations, input and output means may be separated spatially, for example, user inputs can be sent to the medical device via a remote control and the medical device 100 provides outputs for the user via the integrated display 102.

In another embodiment, the display 102 may show selectable sets of user-specific customization data 103-106 for the user to choose from. During an initial customization phase, for example, when a user accesses a medical device for the first time, the user can choose between language packages, which can contain text and/or sound data for adjusting the appearance and/or the functionality of the user interface for controlling the medical device.

According to the invention, the medical device 100 may not provide all requested language data for reducing the amount of required data storage on the medical device. For example, a set of user-specific customization data stored on the medical device 100 may comprise only a part of the requested language data, e.g. only the text data. However, the user may request comprehensive language data, e.g. both text and speech data. The medical device 100 may include computer-readable instructions stored in the memory and executable by the processor to identify the required set of user-specific customization data, for example, text and speech data packages of a specific language. Further, the medical device 100 may include computer-readable instructions stored in the memory and executable by the processor to acquire the required set of the language data from an external data source. Advantageously, the medical device 100 may include computer-readable instructions stored in the memory and executable by the processor to compare the required set of user-specific customization data with the set of user-specific customization data stored on the medical device 100 and compute a delta, i.e. a difference between the required set of user-specific customization data and the set of user-specific customization data stored on the medical device 100. Preferably, only the delta is acquired from the external data source.

In another embodiment, the external data source can be a single server, which can be accessed by the medical device 100 through the network adapter 101 via a local and/or wide area network. Alternatively, or additionally, the external data source can also be a data cloud. In some implementation, at least a part of the user-specific customization data may also be stored on a user token like a USB stick and/or a smart card.

In another embodiment, user authentication can be performed before accessing the medical device 100. The user can verify its identity via an authentication device 107, which may be one or more of smartcard readers, RFID/NFC readers, QR code readers, barcode readers, and/or USB ports. Alternatively, or additionally, a biometric feature can be used for verifying the identity of a user, for example, by using a fingerprint sensor, a retina scanner, a microphone and/or a camera for identifying the user by their voice and/or face. Further embodiments comprise user-specific codes like a user ID, a passphrase, an acoustic and/or electromagnetic signal, which may be generated by an external device such as a remote control, a smartphone, and/or a tablet.

In another embodiment, the required set of user-specific customization data may automatically be acquired in response to verifying the user identity. The user may verify the identity using the authentication device 107. For example, the user may use a smartcard, which can comprise information about the user such as a spoken language, user rights, e.g., limited user rights and/or administrator rights, and/or a user role, e.g., is the user a patient, nurse, or doctor. Depending on the user role and/or user rights, specific functions of the user interface for controlling the medical device can be unlocked and become available, e.g., the user interface may provide a doctor more critical control elements and/or functions than a nurse or patient such as modifying patient prescriptions, adjusting treatment parameters and/or durations, and/or any other action requiring advanced medical knowledge.

Information regarding user profiles associated with a set of the user-specific customization data can be stored on a token and/or carried by a modulated acoustic and/or electromagnetic identification signal sent by a remote control. In some implementations, the information may comprise an identification code and/or text string, e.g., the user ID and/or the username, which can be associated to a specific user profile and/or user role by querying an external data source. For example, within a database, e.g. an SQL database, the identification code and/or the text string can be associated to a user role and/or profile, which may include a set of user-specific customization data such as the preferred language of a user. From the set of requested user-specific customization data and the data stored on the medical device, a required set of customization data is automatically computed and acquired from the same and/or a different external data source.

This implementation is especially advantageous as both the customization of the medical device and the user authentication are automatically combined so that time efficiency can be improved in stressful environments like ICUs.

In another embodiment, at least a part of the user-specific customization data can be stored on a token, e.g., on a USB stick, a Hard-Disk Drive, a Solid State Disk, and/or any other type of movable data storage. For example, in areas where the connection to a wide area and/or local network is limited or interrupted, frequently used customization data, e.g., certain language packages, may be carried on a movable data storage. In some implementations, the token can also be used to verify the identity of a user, e.g., the token may comprise an electronic key, passphrase, code, and/or user ID, for verifying the user identity.

FIG. 2 illustrates an exemplary implementation of a connected-health system according to the present invention. A medical device 200 (e.g. same as the medical device 100 of FIG. 1) may be part of the connected health system.

The medical device 200 may include a network adapter 201, a display 202 for choosing different sets of user-specific customization data 203-206, and an authentication device 207, e.g., a camera. The network adapter 201 may be configured to connect the medical device 200 via a unidirectional and/or bidirectional connection 208 with one or more external servers and/or data clouds 209. The external server and/or the data cloud 209 may store the sets of user-specific customization data and/or can be queried if one of the operating systems of the plurality of medical devices 200, 213-215 requests a required set of user-specific customization data. e.g., in response to the verification of a user identity. For example. a user may access a medical device and/or any other device communicatively connected with the connected health system, e.g., a smartphone, a tablet, and/or a computer, for the first time, and creates a user profile based on a set of user-specific customization data, e.g., language data, and/or user-interface elements and/or functions. In some implementations, via a network adapter and network connection 208, 210-212, the medical device 200, 213-215, can send the set of user-specific customization data to the external server and/or the data cloud 209. Alternatively, or additionally, at least a part and/or some information of the user-specific customization data can be stored on a token such as a USB stick and/or another movable data storage.

In some implementations, a required set of user-specific customization data is acquired from the external server and/or data cloud 209 in response to accessing a second medical device of the connected health system. In some implementations, the required set of user-specific customization data can automatically be acquired by the second medical device in response to verifying the user identity, e.g., via a camera, which may scan the face and/or a body part of the user and employ AI algorithms known in the art to compare the scanned face and/or body part with a stored image and/or video.

The invention claimed is:

1. A computer-implemented method for resource-efficient customization of an operating system of a medical device, the method comprising:

identifying, by the medical device, a first set of user-specific customization data stored on the medical device;

determining, by the medical device, a second set of user-specific customization data that is required by a user;

comparing, by the medical device, the first set of user-specific customization data with the second set of user-specific customization data;

in response to determining that the second set of user-specific customization data is different from the first set of user-specific customization data stored on the medical device:

determining, by the medical device, a delta consisting of one or more items of data present in the second set of user-specific customization data and absent from the first set of user-specific customization data stored on the medical device;

acquiring a first subset of the second set of user-specific customization data from the first set of user-specific customization data stored on the medical device; and acquiring a second subset of the second set of user-customization data from a data storage external to the medical device, the second subset consisting of the delta between the first set of user-specific customization data and the second set of user-specific customization data;

customizing, based on the acquired delta, an output generated by the operating system of the medical device during treatment of the user, wherein customizing the output comprises changing a graphical layout of one or more graphical user interface (GUI) elements during the treatment of the user based on the second subset of the second set of user-customization data acquired from the external data storage; and causing the medical device to provide the customized output to the user.

2. The computer-implemented method of claim 1, further comprising storing the acquired delta on a data storage of the medical device.

3. The computer-implemented method of claim 1, further comprising reading the acquired delta and customizing the operating system of the medical device based at least on the acquired delta.

4. The computer-implemented method of claim 1, wherein the data storage external to the medical device comprises a remote server, a data cloud, and/or a token, wherein the token is or comprises a USB drive, a smart card, a hard-disk drive, and/or a solid-state disk.

5. The computer-implemented method of claim 1, wherein at least a part of the user-specific customization data is stored on a token, and wherein the step of determining, by the medical device, the second set of user-specific customization data comprises reading the token.

6. The computer-implemented method of claim 1, wherein the user-specific customization data comprises language data, the GUI elements, user-specific functions, and/or any combination thereof.

7. The computer-implemented method of claim 6, wherein the language data comprises text and sound.

8. The computer-implemented method of claim 1, wherein the GUI elements comprise user-specific text, buttons, sounds, and/or colors.

9. The computer-implemented method of claim 1, wherein the user-specific customization data further comprises user-specific system rights for controlling the medical device.

10. The computer-implemented method of claim 1, wherein the medical device is configured to provide a renal replacement therapy to a patient, including one or more of Peritoneal Dialysis, Hemodialysis, Hemofiltration, and/or Hemodiafiltration.

11. The computer-implemented method of claim 1, further comprising reading log-in information from the user, wherein the method of claim 1 is triggered at least partly in response to the user having logged in for a first time at the medical device.

12. The computer-implemented method of claim 11, wherein reading the log-in information comprises reading the log-in information via a log-in screen provided by a display of the medical device, and wherein the log-in screen is displayed when the medical device is started and/or woken up from hibernation.

13. The computer-implemented method of claim 1, further comprising providing, by a display of the medical device, different sets of user-specific customization data for the user to select from, wherein the second set of user-specific customization data is the set of user-specific customization data selected by the user.

14. A computer-implemented method for resource-efficient customization of an operating system of a medical device, the method comprising:
  (1) identifying, by the medical device, a first set of user-specific customization data stored on the medical device;
  (2) determining, by the medical device, a second set of user-specific customization data that is required by a user;
  (3) comparing, by the medical device, the first set of user-specific customization data with the second set of user-specific customization data;
  (4) in response to determining that the second set of user-specific customization data is different from the first set of user-specific customization data stored on the medical device:
    determining, by the medical device, a delta consisting of one or more items of data present in the second set of user-specific customization data and absent from the first set of user-specific customization data stored on the medical device;
    acquiring a first subset of the second set of user-specific customization data from the first set of user-specific customization data stored on the medical device; and
    acquiring a second subset of the second set of user-customization data from a data storage external to the medical device, the second subset consisting of the delta between the first set of user-specific customization data and the second set of user-specific customization data;
  (5) customizing, based on the acquired delta, an output generated by the operating system of the medical device during treatment of the user, wherein customizing the output comprises changing a graphical layout of one or more graphical user interface (GUI) elements during the treatment of the user based on the second subset of the second set of user-customization data acquired from the external data storage; and
  (6) causing the medical device to provide the customized output to the user; and
  (7) verifying an identity of the user, before, during, and/or after steps (1) through (6).

15. The computer-implemented method of claim 14, wherein verifying the identity of the user occurs before the steps (1), (2), (3), (4), (5), and (6), and wherein the steps (2), (3), (4), (5), and (6) are automatically triggered in response to verifying the identity of the user.

16. The computer-implemented method of claim 14, wherein verifying the identity of the user is performed via an authentication device of the medical device, the authentication device being or comprising a smartcard reader, an RFID/NFC reader, a QR code reader, a barcode reader, a USB port, a fingerprint sensor, a retina scanner, a microphone and/or a camera.

17. The computer-implemented method of claim 14, wherein verifying the identity of the user is based on multi-factor authentication.

18. The computer-implemented method of claim 14, further comprising reading a user profile after verifying the identity of the user, wherein the user profile comprises information of the second set of user-specific customization data that is required by the user; and wherein, the steps (1), (2), (3), (4), (5), and (6) are automatically triggered in response to reading the information of the second set of user-specific customization data from the user profile.

19. A medical device for resource-efficient customization of an operating system running on the medical device, comprising:

a processor;

a memory; and computer-readable instructions stored in the memory and executable by the processor to:

identify, by the medical device, a first set of user-specific customization data stored on the medical device;

determine, by the medical device, a second set of user-specific customization data that is required by a user;

compare, by the medical device, the first set of user-specific customization data with the second set of user-specific customization data; and in response to determining that the second set of user-specific customization data is different from the first set of user-specific customization data stored on the medical device:

determine, by the medical device, a delta consisting of one or more items of data present in the second set of user-specific customization data and absent from the first set of user-specific customization data stored on the medical device;

acquire a first subset of the second set of user-specific customization data from the first set of user-specific customization data stored on the medical device; and acquire a second subset of the second set of user-customization data from a data storage external to the medical device, the second subset consisting of the delta between the first set of user-specific customization data and the second set of user-specific customization data;

customize, based on the acquired delta, an output generated by the operating system of the medical device during treatment of the user, wherein customizing the output comprises changing a graphical layout of one or more graphical user interface (GUI) elements during the treatment of the user based on the second subset of the second set of user-customization data acquired from the external data storage; and cause the medical device to provide the customized output to the user.

20. A connected-health system for resource-efficient customization of an operating system running on a medical device, comprising:

a data storage external to the medical device;

the medical device, comprising:

a processor;

a memory; and computer-readable instructions stored in the memory and executable by the processor to:

identify, by the medical device, a first set of user-specific customization data stored on the medical device;

determine, by the medical device, a second set of user-specific customization data that is required by a user;

compare, by the medical device, the first set of user-specific customization data with the second set of user-specific customization data; and in response to determining that the second set of user-specific customization data is different from the first set of user-specific customization data stored on the medical device:

determine, by the medical device, a delta consisting of one or more items of data present in the second set of user-specific customization data and absent from the first set of user-specific customization data stored on the medical device;

acquire a first subset of the second set of user-specific customization data from the first set of user-specific customization data stored on the medical device; and acquire a second subset of the second set of user-customization data from a data storage external to the medical device, the second subset consisting of the delta between the first set of user-specific customization data and the second set of user-specific customization data;

customize, based on the acquired delta, an output generated by the operating system of the medical device during treatment of the user, wherein customizing the output comprises changing a graphical layout of one or more graphical user interface (GUI) elements during the treatment of the user based on the second subset of the second set of user-customization data acquired from the external data storage; and cause the medical device to provide the customized output to the user.

* * * * *

UNITED STATES PATENT AND TRADEMARK OFFICE
CERTIFICATE OF CORRECTION

| | | |
|---|---|---|
| PATENT NO. | : 12,159,130 B2 | Page 1 of 1 |
| APPLICATION NO. | : 17/383524 | |
| DATED | : December 3, 2024 | |
| INVENTOR(S) | : Karsten Fischer and Stefan Perplies | |

It is certified that error appears in the above-identified patent and that said Letters Patent is hereby corrected as shown below:

In the Claims

Claim 1
Column 9, Lines 9-10, delete "user-customization data" and insert --user-specific customization data--.
Column 9, Line 21, delete "user-customization data" and insert --user-specific customization data--.

Claim 14
Column 10, Lines 35-36, delete "user-customization data" and insert --user-specific customization data--.
Column 10, Line 47, delete "user-customization data" and insert --user-specific customization data--.

Claim 19
Column 11, Lines 39-40, delete "user-customization data" and insert --user-specific customization data--.
Column 11, Line 51, delete "user-customization data" and insert --user-specific customization data--.

Claim 20
Column 12, Lines 35-36, delete "user-customization data" and insert --user-specific customization data--.
Column 12, Line 47, delete "user-customization data" and insert --user-specific customization data--.

Signed and Sealed this
Twenty-fifth Day of March, 2025

Coke Morgan Stewart
*Acting Director of the United States Patent and Trademark Office*